(12) United States Patent
Meneghini et al.

(10) Patent No.: US 8,414,585 B2
(45) Date of Patent: Apr. 9, 2013

(54) FLEXIBLE TREPHINE AND METHOD OF REMOVING A BOWED IMPLANT FROM A BONE

(75) Inventors: R. Michael Meneghini, Unionville, CT (US); J. Brian Maryan, Martinsville, IN (US)

(73) Assignees: Arthroplasty Innovations, LLC, McCordsville, IN (US); Medvation, Incorporated, Martinsville, IN (US)

( * ) Notice: Subject to any disclaimer, the term of this patent is extended or adjusted under 35 U.S.C. 154(b) by 0 days.

(21) Appl. No.: 12/449,490

(22) PCT Filed: Feb. 12, 2008

(86) PCT No.: PCT/US2008/001812
§ 371 (c)(1),
(2), (4) Date: Aug. 11, 2009

(87) PCT Pub. No.: WO2008/100484
PCT Pub. Date: Aug. 21, 2008

(65) Prior Publication Data
US 2010/0094361 A1    Apr. 15, 2010

Related U.S. Application Data

(60) Provisional application No. 60/900,983, filed on Feb. 13, 2007.

(51) Int. Cl.
*A61B 17/16* (2006.01)
(52) U.S. Cl. ........................................ 606/79; 606/86 R
(58) Field of Classification Search ............... 606/79–85
See application file for complete search history.

(56) References Cited

U.S. PATENT DOCUMENTS

| 4,696,308 | A | | 9/1987 | Meller et al. |
| 5,807,241 | A | * | 9/1998 | Heimberger ................... 600/142 |
| 6,053,922 | A | | 4/2000 | Krause et al. |
| 6,264,657 | B1 | * | 7/2001 | Urbahns et al. ............... 606/914 |
| 6,447,518 | B1 | | 9/2002 | Krause et al. |
| 2002/0116007 | A1 | | 8/2002 | Lewis |
| 2010/0086898 | A1 | * | 4/2010 | Bagambisa ................... 433/173 |

OTHER PUBLICATIONS

Notification Concerning Transmittal of International Preliminary Report on Patentability and International Preliminary Report on Patentability issued on Aug. 19, 2009 in corresponding PCT Patent Application No. PCT/US2008/01812.
International Search Report mailed on Jul. 11, 2008 for the corresponding International patent application No. PCT/US08/01812.
Matthew S. Austin, MD, et al., Previously Unreported Complication of Trephine Reamers in Revision Total Hip Arthroplasty, The Journal of Arthroplasty, vol. 21, No. 2 (Feb. 2006) pp. 299-300.

(Continued)

*Primary Examiner* — Nicholas Woodall
(74) *Attorney, Agent, or Firm* — Posz Law Group, PLC

(57) ABSTRACT

A flexible trephine includes a flexible section that is formed of a spring member. The trephine is tubular and includes a central passage so that the trephine can coaxially fit over a longitudinal implant while force is applied to the trephine. The trephine has an annular cutting head for removing bone that surrounds the implant, so that the implant can be removed. The trephine is urged in the longitudinal direction of the implant while fitted coaxially on the implant so that the implant can be separated from the bone. The flexible section of the trephine allows the trephine to conform to and follow a bowed implant. The cutting head can include multiple teeth or a single osteotome.

11 Claims, 5 Drawing Sheets

OTHER PUBLICATIONS

Bassam A. Masri, MD, FRCSC, et al., Removal of Solidly Fixed Implants During Revision Hip and Knee Arthroplasty, Journal of the American Academy of Orthopaedic Surgeons, vol. 13, No. 1 (Jan./Feb. 2005) pp. 18-27.

Wayne G. Paprosky, MD, et al., Component Removal in Revision Total Hip Arthroplasty, Clinical Orthopaedics and Related Research, No. 393 (Dec. 2001) pp. 181-193, © 2001 Lippincott Williams & Wilkins, Inc.

* cited by examiner

US 8,414,585 B2

FLEXIBLE TREPHINE AND METHOD OF REMOVING A BOWED IMPLANT FROM A BONE

BACKGROUND OF THE INVENTION

The present invention relates to a trephine for component removal in total hip arthroplasty. More particularly, the invention relates to a flexible trephine for removal of bowed prosthesis components.

Removing well-fixed femoral components, particularly cementless components, in revision total hip arthroplasty is often required for recurrent hip instability, sepsis or mechanical failure. If the cementless femoral component is of a fully porous-coated design that has obtained distal osseointegration in the femoral isthmus and diaphysis, then the implant must be transected with a metal cutting device (not illustrated) at the junction of the proximal tapered portion and the distal cylindrical portion. Once transected, the proximal portion is removed from the femur. Then, a rigid, hollow, cylindrical trephine (not illustrated), which is rotated manually or by a machine, is used to disrupt the component-bone interface and remove the distal stem. That is, the trephine is fitted in a coaxial fashion over the stem while being rotated and urged in the longitudinal direction to remove bone and separate the stem from the femur.

Recently, a variety of bowed, fully-porous coated stems 414 for femoral prosthesis components 412 have become available to accommodate the anatomic bow of the femoral canal in the sagittal plane. See FIG. 4. These stems 414 are useful in situations where proximal bone loss is present and distal fixation is required in the femoral diaphysis where the bowed shape of the femur 422 would often prove a difficult match for a straight stem. Bowed implant stems 414 are being used with increasing frequency. Unfortunately, there are currently no proven methods for removing a well-fixed bowed fully porous-coated stem, as the currently available cylindrical trephines are straight (linear) and non-flexible and would fail to progress distally over a bowed implant 412. The difficulty of removing bowed implants 412 discourages their use by some surgeons.

SUMMARY OF THE INVENTION

Basically, the invention is a trephine that includes a tubular body. The tubular body includes a flexible section formed by a spring member, and the tubular body is constructed to fit coaxially over an implant. Further, the trephine includes an annular cutting head fixed to a distal end of the tubular body. When a force is applied to a proximal end of the trephine, the tubular body transmits the force to the cutting head for removing the implant from a bone.

In a further aspect of the invention, the flexible section is formed by a helical spring.

In a further aspect of the invention, the implant is a femoral component of a hip prosthesis, and the tubular body includes a central passage. The central passage is sized to accommodate a distal portion of a stem of the femoral component.

In a further aspect of the invention, the spring member is constructed such that the flexible section conforms to and follows a bowed stem of a femoral component of a hip prosthesis while the trephine is rotated and urged in a longitudinal direction of the bowed stem.

In a further aspect of the invention, the proximal end of the trephine includes a coupler for coupling the trephine to a driver for applying torque to the trephine.

In a further aspect of the invention, the proximal end of the trephine has an impact receiving surface, which is adapted to receive an axial impact and to transmit the axial impact to the trephine.

In a further aspect of the invention, the distal end of the trephine includes a plurality of teeth for cutting bone that surrounds the implant.

In a further aspect of the invention, the distal end of the trephine includes an osteotome for cutting bone that surrounds the implant.

The invention includes a method of removing a bowed implant from a bone, and the method includes placing a flexible trephine over one end of the implant and applying force to the trephine to remove bone surrounding the implant. The method further includes urging the trephine coaxially along the length of the implant to cause the trephine to bend and follow the curvature of the bowed implant while force is applied to the trephine. Then, the implant is removed from the femur.

In a further aspect of the method of the invention, the application of force includes applying torque to the trephine for rotating the trephine about its longitudinal axis.

In a further aspect of the method of the invention, the implant is a part of a femoral component of a hip prosthesis.

BRIEF DESCRIPTION OF THE DRAWINGS

The accompanying figures, together with the detailed description below, are incorporated in and form part of the specification, serve to further illustrate various embodiments and to explain various principles and advantages all in accordance with the present invention.

DETAILED DESCRIPTION OF THE PREFERRED EMBODIMENTS

Figure 1:
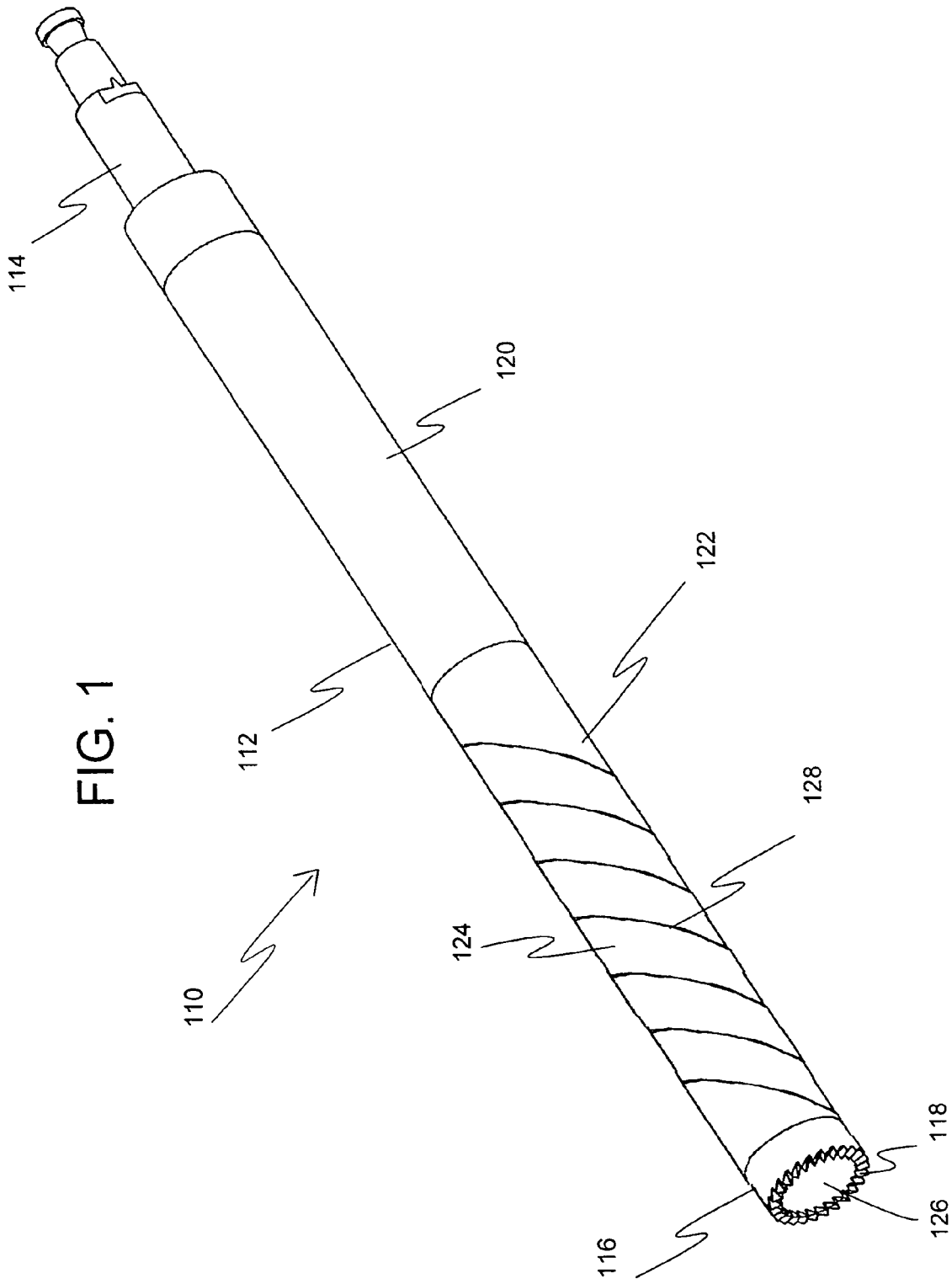
FIG. 1 is a perspective view of the flexible trephine of the present invention.

FIG. 1 shows a flexible trephine 110 including a body 112, a coupling 114 and a cutting head 116. The trephine 110 is preferably made entirely of stainless steel. The cutting head 116 and the body 112 are cannulated, or tubular, such that an interior passage 126 is formed in the trephine 110. The interior passage 126 permits the cutting head 116 and the body 112 to coaxially fit over and follow a bowed distal portion 414 of a femoral implant 412 (See FIG. 4). During a procedure to remove the implant 412, for example, the entire trephine 112 is rotated so that teeth 118 of the cutting head 116 can remove bone that surrounds the distal portion 414 of the implant 412. Thus, the flexible trephine 110 facilitates the removal of a bowed implant 412.

The coupling 114 is provided to facilitate coupling of the trephine 110 to a rotating machine (not illustrated) or a manual device for applying torque to the trephine 110 in a manner well-known in the art. Thus, during use, the trephine 110 is rotated about its longitudinal axis. The coupling 114 that is shown in the illustrated embodiment of FIG. 1 is known as a Hudson coupling. However, any of numerous known couplings, including simple threads, can be employed according to the needs of surgeons.

The body 112 includes a proximal section 120, which is tubular and rigid. In the embodiment of FIG. 1, the proximal section 120 is linear and not flexible. The proximal section 120 is attached at its proximal end to a distal end of the coupling 114.

The body 112 includes a flexible section 122 formed by a spring member 124, or flexing means, such that the flexible section 122 can bend to conform to the shape of the curved implant stem 414 while fitted coaxially on the stem 414. In the illustrated embodiment, the flexible section 122 is located between the proximal section 120 and the cutting head 118. Thus, in the illustrated embodiment, the distal end of the trephine 110 is flexible. Alternatively, the entire body 112 can be formed by a spring-like member such that the entire body 112 is flexible.

The spring member 124 of FIG. 1 is formed by cutting at least one helical slot 128 so that the slot 128 passes entirely through the cylindrical wall that forms the flexible section 122. The number of helical slots and the angle of each helical slot are selected to achieve the desired flexibility and torque transmitting characteristics, as is well understood by one of ordinary skill in the art. Similarly, the thickness of the tubular wall forming the flexible section 122 is selected to achieve the desired flexibility and torque transmission characteristics. In the illustrated embodiment, the wall thickness of the flexible section 122 is approximately 2.0 mm.

An annular cutting head 116 is fixed to a distal end of the tubular body 112. When torque is applied to the proximal end of the trephine 110, through the coupling 114, the tubular body 112 transmits the torque to the cutting head 116 for removing bone surrounding an implant stem 414.

The diameter of the interior passage 126 is selected according to the diameter of the distal portion of the stem being removed, and the trephine 110 can be made in several sizes to accommodate the varying sizes of implants in existence. For example, the diameter of the interior passage 126 can range from approximately 9 mm to 22.5 mm. The surgeon selects a trephine 110 that has the desired clearance between the implant and the inner surface of the body 112. Choosing a trephine 110 that is too small in diameter will create excessive friction and binding between the implant and the trephine 110. Choosing a trephine 110 that is too large in diameter will remove too much bone.

The lengths of existing implants vary. Therefore, the length of the trephine 110 can vary accordingly. However, in one embodiment, the length of the trephine 110 is approximately 270 mm.

The coupling 114 can be fastened to the proximal section 120 by welding or other known fastening methods. Similarly, the proximal section 120 can be fastened to the flexible section 122 and the cutting head 116 can be fastened to the flexible section 122 by welding or other known fastening methods. If welding is used, it is preferred to use low temperature welding such as electron beam welding to avoid distortion of the stainless steel forming the components.

In one embodiment, the coupling 114 is attached to the proximal section 120 but is removable and replaceable. Thus, if the trephine 110 becomes jammed during a procedure, the coupling can be removed, and an object can be pushed into the hollow center of the body 112 and against the implant to separate the trephine 110 from the implant. Further, when the coupling 114 is removable, the coupling 114 can be easily replaced with the same or another type of coupling.

Figure 2:
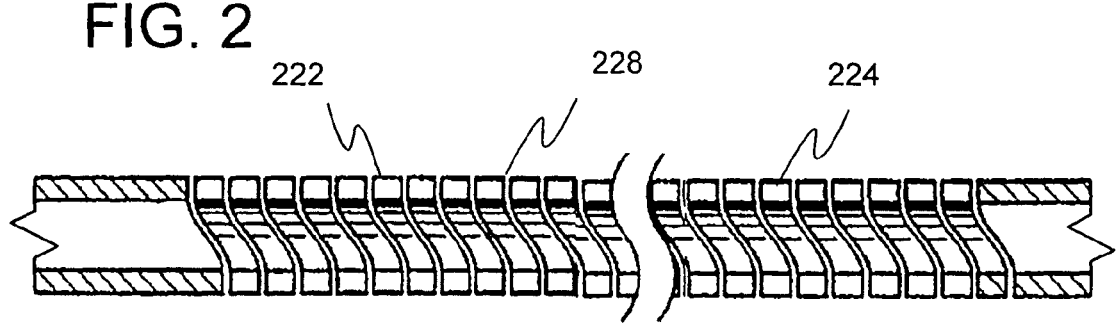
FIG. 2 is a cross sectional view of the flexible section of a second embodiment of the flexible trephine.

Any of numerous known flexible shafts that can transmit torque without buckling or twisting can be employed in the flexible section 122. For example, FIG. 2 shows an alternate flexible section 222, which is a variation of the flexible section 122 of FIG. 1. In the second embodiment of FIG. 2, only the flexible section 222 differs from the trephine 110 shown in FIG. 1. The flexible section 222 of the second embodiment includes an alternate spring member 224 that is formed by cutting a slot 228 in a helical pattern, the angle of which differs from that of the embodiment of FIG. 1.

Figure 3:
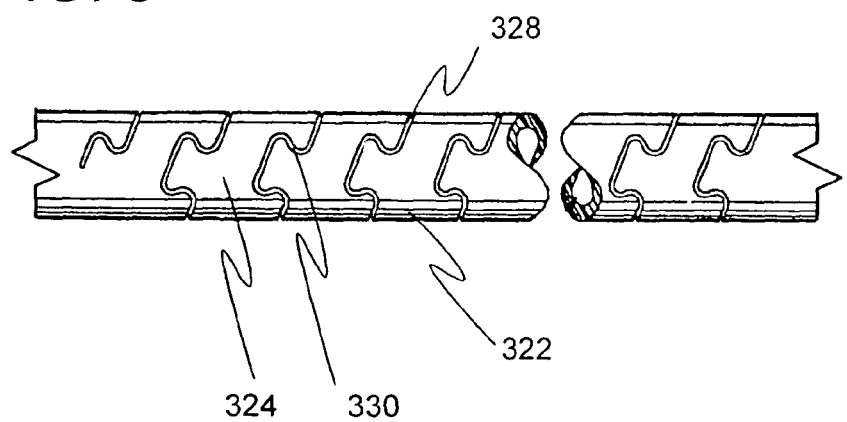
FIG. 3 is a partial side view of the flexible section of a third embodiment of the flexible trephine.

In a third embodiment, as shown in FIG. 3, the flexible section 122 of the embodiment of FIG. 1 is replaced by an alternate flexible section 322, which includes an alternate spring member 324. The alternate spring member 324 is formed by a slot 328 that is cut in the flexible section 322 in a generally helical pattern that includes curves 330 that form regular dovetail patterns as shown in FIG. 3. This pattern permits torque to be transmitted effectively in either a clockwise or a counterclockwise direction. This embodiment is preferred due to its favorable torque transmission characteristics. A flexible shaft like to that shown in FIG. 3 is shown in U.S. Pat. Nos. 6,053,922 and 6,447,518 to Krause et al. and is commercially available from Nemcomed, Inc. of Hicksville, Ohio, USA.

In removing a femoral component 412 of a hip prosthesis, the surgeon first cuts through the femoral component at a junction 416 between a proximal portion 418 and a distal portion 414 to remove the proximal end 418 of the femoral component 412. Then, the trephine 110 is placed over the remaining distal portion, or stem 414, of the femoral component 412. The trephine 110 is driven to rotate by a motorized or manually operated mechanical driver (not illustrated). The trephine 110 is then urged over the stem 414 in a coaxial fashion such that bone surrounding the stem is removed by the cutting head 118. In the case of a bowed stem 414 of a femoral component 412, the flexible section 122 conforms to and follows the shape of the bowed stem 414 while moving along the length of the stem 414 longitudinally and while rotating. Thus, torque is transmitted to the cutting head 118 even while the trephine 110 flexes or bends to follow the bowed stem 414.

Figure 6:
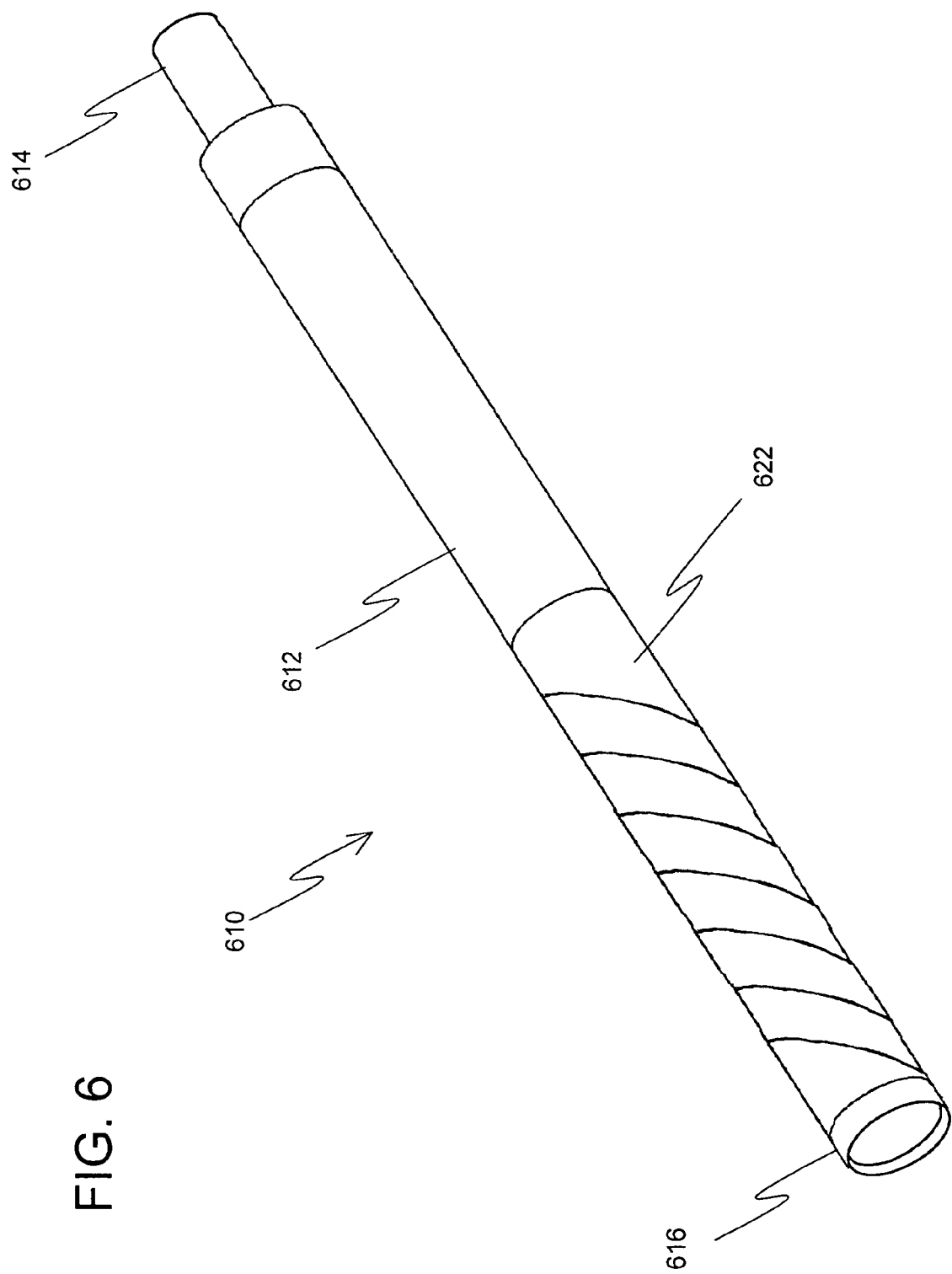
FIG. 6 is a perspective view of a further embodiment of a flexible trephine of the present invention.

FIG. 6 shows a further embodiment. A flexible trephine 610 of FIG. 6 includes a body 612, an impact receiving member 614 and a cutting head 616. The flexible trephine 610 differs from the flexible trephine 110 of FIG. 1 only in that the cutting head 618 is a hollow cylindrical osteotome having a single beveled cutting edge and the proximal end of the flexible trephine 610 includes an impact receiving member 614, which can be struck by a surgeon to apply axial force to the trephine 610. Thus, a flexible section 622 of the trephine 610 is the same as the flexible section 122 of the embodiment of FIG. 1, which permits the flexible trephine 610 to conform with and follow a curved implant part such as the bowed stem 414. The flexible trephine 610 of FIG. 6 is used in a manner similar to that described above in connection with the flexible trephine 110 of FIG. 1 except that cutting is primarily done by application of axial force rather than torque, and there is no need to attach a mechanical driver to the proximal end of the trephine 610.

Although the trephine 110 is described primarily in the context of removing a femoral component, the trephine 110 of the illustrated embodiments can be used to remove other components such as tibial components and shoulder implants.

Although the trephine 110 is discussed as an assembly of parts, the coupling 114, the proximal section 120, the flexible section 124, and the cutting head, the trephine 110 can be manufactured as a single, unitary part if desired.

The trephine 110 is primarily to be used to remove cementless components. However, the trephine may also be used to disrupt the cement-bone interface between a cemented component and a bone.

Figure 4:
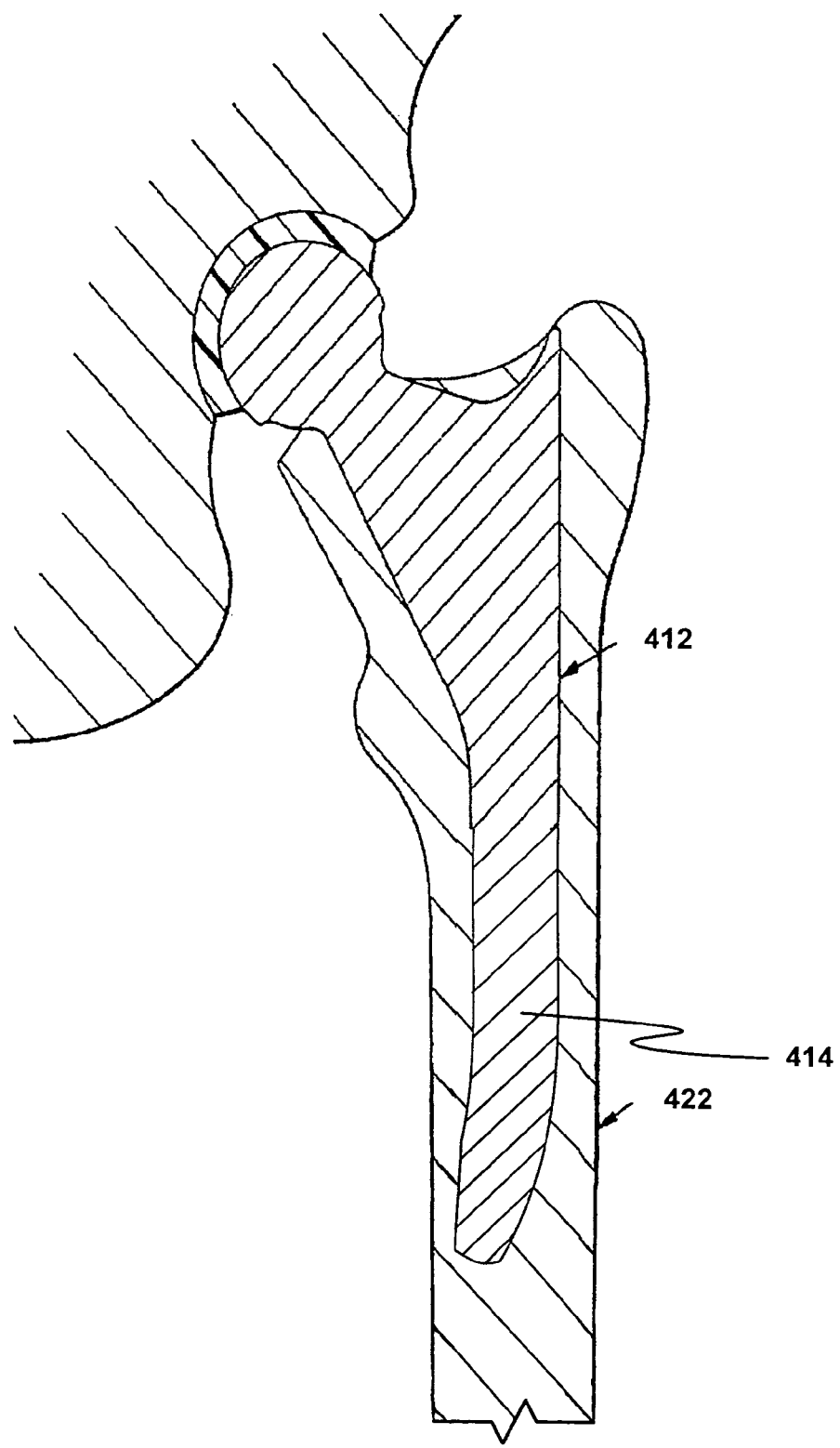
FIG. 4 is a cross sectional view of a bowed femoral implant.
Figure 5:
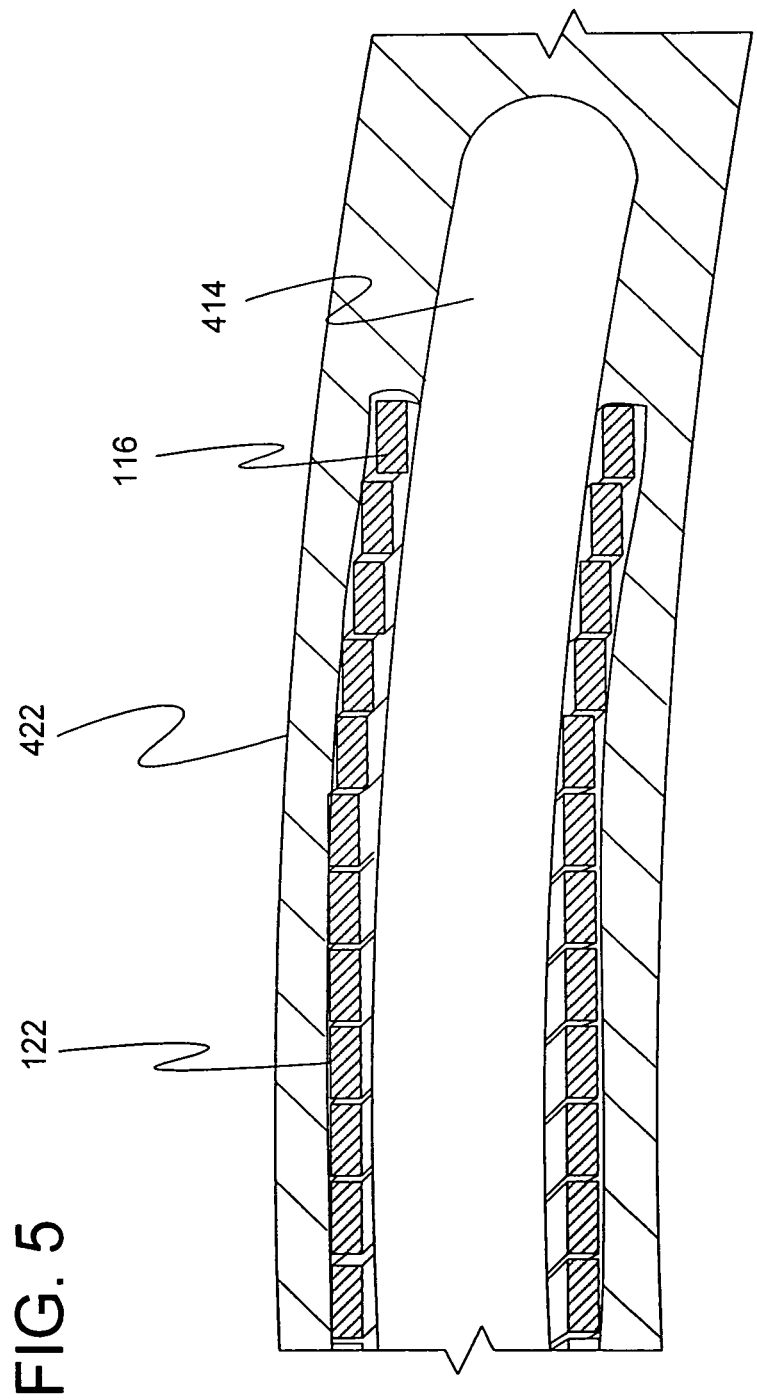
FIG. 5 is a cross sectional view of a femoral implant being separated from a femur by an exemplary flexible trephine of the present invention.

Although the flexible trephine 110 is primarily for removal of bowed implant stems such as the bowed stem 414 of FIG. 4, the flexible trephine 110 may also be used to remove straight (substantially linear) implant stems. The flexibility may prevent binding that sometimes occurs between a rigid trephine and a straight implant stem.

Although the flexible trephine of the illustrated embodiments is primarily for removal of prosthesis components, it can also be used to remove other types of implants, such as surgical nails and screws.

This disclosure is intended to explain how to fashion and use various embodiments in accordance with the invention rather than to limit the true, intended, and fair scope and spirit thereof. The foregoing description is not intended to be exhaustive or to limit the invention to the precise form disclosed. Modifications or variations are possible in light of the above teachings. The embodiments were chosen and described to provide the best illustration of the principles of the invention and its practical application, and to enable one of ordinary skill in the art to use the invention in various embodiments and with various modifications as are suited to the particular use contemplated. All such modifications and variations are within the scope of the invention as determined by the appended claims, as may be amended during the pendency of this application for patent, and all equivalents thereof, when interpreted in accordance with the breadth to which they are fairly, legally, and equitably entitled.

The invention claimed is:

1. A trephine comprising:
   a tubular body, including
   a linear, rigid section, and
   a flexible section formed by a spring member,
   the tubular body being constructed to fit coaxially over an implant; and
   an annular cutting head fixed to an end of the flexible section that is not connected with the rigid section, wherein,
   when a force is applied to an end of the tubular body that includes an end of the rigid section that is not connected to the flexible section, the force is transmitted through the rigid section and the flexible section to the cutting head, such that the annular cutting head is operable to remove bone surrounding the implant, and
   the spring member is constructed such that when the implant is bowed, the flexible section conforms to and follows the bowed implant while the trephine is rotated and urged in a longitudinal direction of the bowed implant.

2. The trephine according to claim 1, wherein the flexible section is formed as a helical spring.

3. The trephine according to claim 1, wherein
   the implant is a femoral component of a hip prosthesis,
   the tubular body includes a central passage, and
   the central passage is sized to accommodate a distal portion of a stem of the femoral component.

4. The trephine according to claim 1, further comprising:
   a coupler connected to the body at the end of the body that includes the end of the rigid section that is not connected to the flexible section, wherein
   the coupler couples the trephine to a driver that applies torque as the force that is transmitted to the cutting head.

5. The trephine according to claim 1, further comprising:
   an impact receiving member, which is adapted to receive an axial impact on an impact receiving surface, wherein
   an axial force is applied as the force that is transmitted to the cutting head.

6. The trephine according to claim 1, wherein
   the cutting head includes a plurality of teeth for cutting bone that surrounds the implant.

7. The trephine according to claim 1, wherein
   the distal end of the trephine includes an osteotome for cutting bone that surrounds the implant.

8. The trephine according to claim 1, wherein
   the annular cutting head being operable to remove bone surrounding the implant includes being operable to disrupt a component-bone interface.

9. A method of removing a bowed implant from a bone comprising:
   placing a trephine with a rigid portion and a flexible portion over one end of the bowed implant;
   applying a force to the trephine to thereby remove bone surrounding the bowed implant;
   urging the trephine coaxially along the length of the bowed implant thereby causing the flexible portion to bend and conform to the bowed implant while the force is applied to the trephine; and
   removing the implant from the femur.

10. The method of claim 9, wherein
    the application of force includes applying torque to rigid portion of the trephine thereby rotating the trephine about its longitudinal axis.

11. The method of claim 9, wherein
    the placing includes placing the flexible trephine over one end of a part of a femoral component of a hip prosthesis.

\* \* \* \* \*